United States Patent [19]
DeGroot

[11] Patent Number: 6,167,308
[45] Date of Patent: Dec. 26, 2000

[54] CLOSED LOOP ATP

[75] Inventor: Paul J. DeGroot, Brooklyn Park, Minn.

[73] Assignee: Medtronic, Inc., Minneapolis, Minn.

[21] Appl. No.: 09/289,307

[22] Filed: Apr. 9, 1999

[51] Int. Cl.$^7$ .................................................. A61N 1/362
[52] U.S. Cl. ............................................................ 607/14
[58] Field of Search .................................. 607/4, 5, 6, 7, 607/8, 14, 9

[56] References Cited

U.S. PATENT DOCUMENTS

| | | |
|---|---|---|
| 4,407,288 | 10/1983 | Langer et al. . |
| 4,428,378 | 1/1984 | Anderson et al. . |
| 4,821,723 | 4/1989 | Baker, Jr. et al. . |
| 4,830,006 | 5/1989 | Haluska et al. . |
| 4,865,036 | 9/1989 | Chirife . |
| 4,967,747 | 11/1990 | Carroll et al. . |
| 5,176,137 | 1/1993 | Erickson et al. . |
| 5,209,229 | 5/1993 | Gilli . |
| 5,251,624 | 10/1993 | Bocek et al. . |
| 5,330,505 | 7/1994 | Cohen . |
| 5,662,688 | 9/1997 | Haefner et al. . |
| 5,836,971 | 11/1998 | Starkweather . |
| 5,846,263 | 12/1998 | Peterson et al. . |
| 5,855,593 | 1/1999 | Olson et al. . |

OTHER PUBLICATIONS

"Characterization of return cycle responses predictive of successful pacing–mediated termination of ventricular tachycardia" by Callans et al, published in the *Journal of American College of Cardiology*, vol. 25, No. 1, Jan., 1995, pp 47–53.

*Primary Examiner*—Scott M. Getzow
*Attorney, Agent, or Firm*—Reed A. Duthler; Girma Wolde-Michael; Harold R. Patton

[57] ABSTRACT

An implantable anti-tachycardia pacemaker having the capability of switching from a first pacing regimen to a second pacing regimen, without waiting to determine whether the first pacing regimen actually is successful in terminating the tachycardia. The device first delivers a short series of pacing pulses at the defined parameters of the first pacing regimen and then interrupts delivery of pacing pulses and measures the return cycle of the subsequent spontaneous depolarization. The device then resumes delivery of the first pacing regimen for a second, greater number of pacing pulses and again measures the return cycle. In the event that no increase in the return cycle occurs following the delivery of the longer series of pacing pulses, the device terminates the pacing regimen presently underway, and initiates the next scheduled therapy. In the event that an increase in the return cycle is detected, the device may simply deliver the programmed number of pacing pulses defined for the first pacing regimen.

10 Claims, 3 Drawing Sheets

CLOSED LOOP ATP

BACKGROUND OF THE INVENTION

The present invention relates to implantable heart stimulators generally, and more particularly to implantable anti-tachycardia pacemakers.

Typically, implantable anti-tachycardia pacemakers have the capability of providing a variety of anti-tachycardia pacing regimens. Normally, these regimens are applied according to a pre-programmed sequence, and each extends over a series of predetermined number of pacing pulses. After the series of pacing pulses is delivered, the devices check to determine whether the series of pulses was effective in terminating the detected tachyarrhythmia. Typically, termination is confirmed by a return to sinus rhythm, for example in response to a sequence of a predetermined number of spontaneous depolarizations separated by greater than a defined interval. In the absence of detected termination, delivery of a subsequent series of pacing pulses having modified pulse parameters, e.g. reduced inter-pulse interval, occurs in response to a redirection of tachycardia, using criteria similar to that employed to originally detect tachycardia, but in most cases based on less stringent criteria. Devices which function according to the basic methodology described above are disclosed in U.S. Pat. No. 4,830,006 issued to Haluska et al., U.S. Pat. No. 5,836,971 issued to Starkweather and U.S. Pat. No. 5,846,263 issued to Peterson et al.

SUMMARY OF THE INVENTION

The present invention is directed to an implantable anti-tachycardia pacemaker which may modify its therapy regimen at an earlier point during delivery of a series of pacing pulses than is typically allowed, in response to a determination that the series of pacing pulses, if continued, would be unlikely to terminate the detected tachycardia. Rather than simply delivering the entire series of pacing pulses, the device initially delivers only a few pulses having the parameters defined for the scheduled pacing regimen and then determines whether the series of pulses, if continued, would likely result in termination of the tachycardia. If the device determines that termination would likely occur, the device may the proceed to deliver the entire series of pulses. If the device determines that the series of pulses, if continued, would likely not result in termination of the tachycardia either a new anti-tachycardia pacing regimen having modified pulse parameters may be employed or the device may deliver a high energy cardioversion pulse. For example, a defined anti-tachycardia pacing regimen may employ a series of pulses separated by a first interval, either preprogrammed or determined as a function of the rate of the detected tachycardia. The series of pulses as programmed may extend over 20 or more pulses, for example, but the device according to the present invention is configured to allow a determination after the first few pulses of the relative likelihood that the series of pulses if completed would actually terminate the tachycardia.

As set forth in the article, "Characterization of return cycle responses predictive of successful pacing-mediated termination of ventricular tachycardia" by Callans et al, published in the *Journal of American College of Cardiology*, Vol. 25, No. 1, January, 1995, pp 47–53, the return cycles (the time periods between a delivered anti-tachycardia pacing pulse and the next subsequent spontaneous depolarization) after just a few beats of a series of overdrive pacing pulses can be predictive of the likelihood of success of a longer series of overdrive pacing pulses having the same parameters. The inventors of the present application have employed this principle in the context of an implantable anti-tachycardia pacemaker in order to allow the device to switch from a first pacing regimen to a second pacing regimen, without waiting to determine whether the first pacing regimen actually is successful in terminating the tachycardia. In order to accomplish this result, the device first delivers a short series of pacing pulses at the defined parameters of the pacing pulse regimen, for example two to four pulses, and then interrupts delivery of pacing pulses to await the next spontaneous depolarization. The device then resumes delivery of the pacing pulse regimen for a second, greater number of pacing pulses, for example three to six pulses, and again measures the return cycle. In the event that no increase in the return cycle occurs following the delivery of the longer series of pacing pulses, the device terminates the pacing pulse regimen presently underway, and initiates the next scheduled therapy, which may be a pacing pulse regimen, preferably at a shorter inter-pulse interval or a cardioversion shock. In the event that an increase in the return cycle is detected, the device may simply deliver the number of pacing pulses defined for the pacing pulse regimen. Optionally, particularly in cases in which longer series of pacing pulses are programmed for a pacing regimen, the device may repeat the test for return cycle prolongation prior to switching to the next scheduled therapy or delivering number of pacing pulses defined for the pacing pulse regimen.

DETAILED DESCRIPTION OF THE PREFERRED EMBODIMENTS

Figure 1:
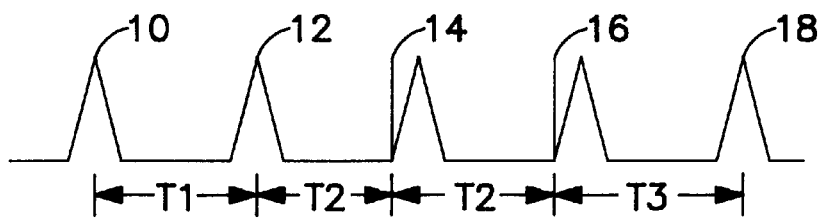
FIGS. 1 and 2 are simulated EKG strips illustrating the operation of a device according to the present invention.
Figure 2:
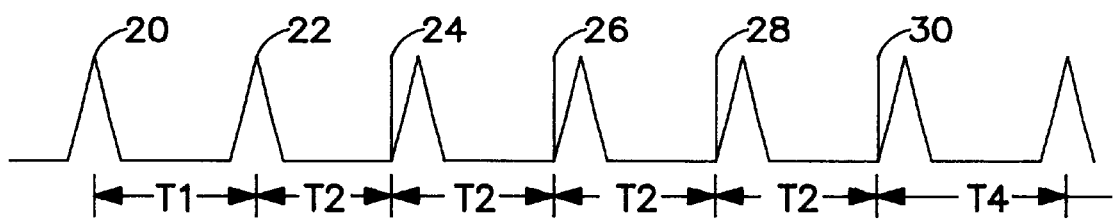

FIGS. 1 and 2 are simulated electrocardiograms illustrating operation of the device as it operates to determine whether a pacing regimen is likely to successfully terminate a tachycardia. R-waves 10 and 12, indicative of the ongoing tachycardia are separated by an interval T1, corresponding to the rate of the detected tachycardia. A short series of anti-tachycardia pacing pulses 14 and 16 are delivered, separated by intervals T2, which are determined as a function of the duration of intervals T1 separating preceding R-waves during the tachycardia. In order to determine whether a series of overdrive pacing pulses separated by intervals T2 is likely to be effective, the device waits after delivery of the second pulse 16 and measures the time T3 to the next spontaneous R-wave 18. Either immediately following spontaneous R-wave 18, or following a short sequence of additional spontaneous R-waves 20 and 22, the device delivers a second series of a greater number of anti-tachycardia pacing pulses 24, 26, 28 and 30 separated by intervals T2. The device then suspends delivery of the anti-tachycardia pacing pulses and measures the return cycle T4. Depending upon the relationship of return cycle T4 and T3, the device then either continues delivery of pacing pulses separated by intervals T2 or switches to different therapy. In particular, if return cycle T4 is not greater than return cycle T3, by a pre-defined increment e.g. >0 to 200 ms, a new anti-tachycardia pacing pulse regimen may be initiated preferably having an inter-pulse interval somewhat less than T2. The new pacing therapy may be initiated immediately or following a few spontaneous depolarizations in order that the inter-depolarization intervals of the tachycardia can be re-measured. Alternatively, charging of the high voltage output capacitors of the device may be initiated in order to allow delivery of a cardioversion shock. If the second return interval T4 is greater than return interval T3 by the defined increment, the device resumes delivery of anti-tachycardia pacing pulses separated by time intervals T2. The device may then simply deliver the entire programmed number of anti-tachycardia pacing pulses for the pacing regimen. If the pacing regimen as programmed extends over or a relatively large number of pulses, the device may optionally measure the return cycle an additional time, repeating the process described above, prior to delivery of the entire programmed number of pacing pulses or initiating deliver of a new therapy.

Figure 3:
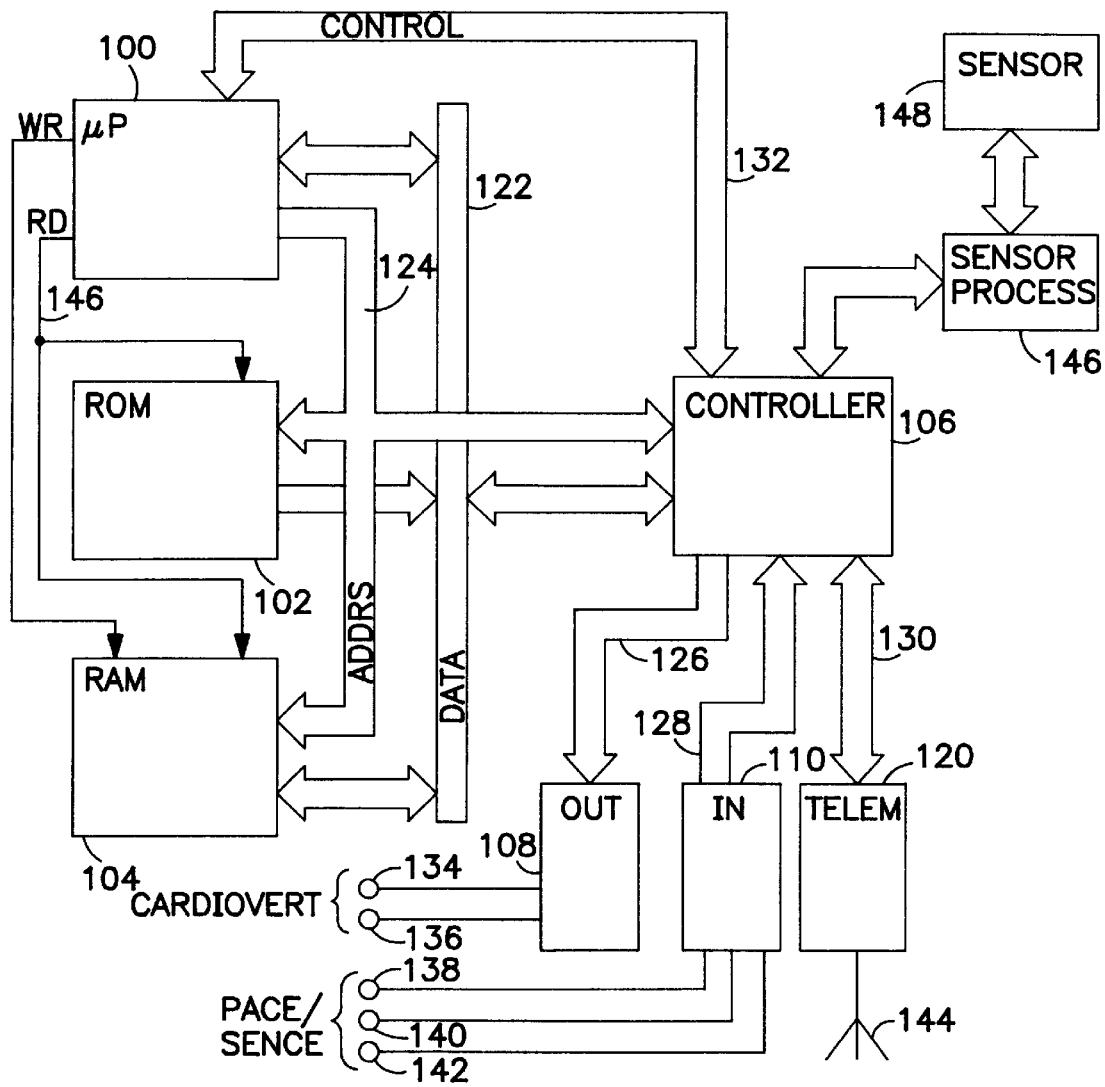
FIG. 3 is a block, functional diagram of a device according to the present invention.

FIG. 3 is a block, functional diagram of an illustrative embodiment of a cardioverter/pacemaker according to the present invention. As illustrated, the device is embodied as a microprocessor based stimulator. However, other digital circuitry embodiments and analog circuitry embodiments are also believed to be within the scope of the invention. For example, devices having general structures as illustrated in U.S. Pat. No. 5,251,624 issued to Bocek et al., U.S. Pat. No. 5,209,229 issued to Gilli, U.S. Pat. No. 4,407,288, issued to Langer et al, U.S. Pat. No. 5,662,688, issued to Haefner et al., U.S. Pat. No. 5,855,893, issued to Olson et al., U.S. Pat. No. 4,821,723, issued to Baker et al. or U.S. Pat. No. 4,967,747, issued to Carroll et al., all incorporated herein by reference in their entireties may also be usefully employed in conjunction with the present invention. Similarly, while the device of FIG. 3 takes the form of a ventricular pacemaker/cardioverter, the present invention may also be usefully be employed in a device having atrial pacing and cardioversion capabilities. FIG. 3 should thus be considered illustrative, rather than limiting with regard to the scope of the invention.

The primary elements of the apparatus illustrated in FIG. 3 are a microprocessor 100, read only memory 102, random access memory 104, a digital controller 106, input and output amplifiers 110 and 108 respectively, and a telemetry/programming unit 120.

Read only memory stores the basic programming for the device, including the primary instruction set defining the computations performed to derive the various timing intervals employed by the cardioverter. Random access memory 104 serves to store variable control parameters, such as programmed pacing rate, programmed cardioversion intervals, pulse widths, pulse amplitudes, and so forth which are programmed into the device by the physician. Random access memory 104 also stores derived values, such as the stored time intervals separating tachyarrhythmia pulses and the corresponding high rate pacing interval. Reading from random access memory 104 and read only memory 102 is controlled by RD line 146. Writing to random access memory 104 is controlled by WR line 148. In response to a signal on RD line 146, the contents of the random access memory 104 or read only memory 102 designated by the then present information on address bus 124 are placed on data bus 122. Similarly, in response to a signal on WR line 148, information on data bus 122 is written into random access memory 104 at the address specified on the address bus 124.

Controller 106 performs all of the basic control and timing functions of the device. Controller 106 includes at least one programmable timing counter, initiated on ventricular contractions, and timing out intervals thereafter. This counter is used to generate the basic timing intervals referred to above and to measure intervals ending in intrinsic depolarizations. On time out of the pacing escape interval or in response to a determination that a cardioversion or defibrillation pulse is to be delivered, controller 106 triggers the appropriate output pulse from output stage 108, as discussed below. Following generation of stimulus pulses controller 106 generates corresponding interrupts on control bus 132, waking microprocessor 100 from its sleep state, allowing it to perform any required mathematical calculations, including all operations associated with evaluation of return cycle times and selection of anti-tachyarrhythmia therapies according to the present invention. The timing counter in controller 106 also times out a ventricular refractory period, as discussed below. The time intervals which the timing counter in controller 106 counts prior to time-out are controlled via data from RAM 104, applied to the controller 106 via data bus 122.

Controller 106 also generates wake-up interrupts for microprocessor 100 on the occurrence of sensed ventricular contractions. On occurrence of a sensed ventricular contraction, in addition to an interrupt indicating its occurrence placed on control bus 132, the then current value of the timing counter within controller 106 is placed onto data bus 122, for use by microprocessor 100 in determining whether a tachyarrhythmia is present and for determining the intervals separating individual tachyarrhythmia beats.

Output stage 108 contains a high output pulse generator capable of generating cardioversion pulses of at least 0.1 joules, to be applied to the patient's heart via electrodes 134 and 136, which are typically large surface area electrodes mounted on or in the heart or located subcutaneously. Other electrode configurations may also be used, including three or more electrodes arranged within and around the heart. Typically the high output pulse generator includes high voltage capacitor, a charging circuit and a set of switches to allow delivery of monophasic or biphasic cardioversion or defibrillation pulses to the electrodes employed. Output circuit 108 also contains a pacing pulse generator circuit which is also coupled to electrodes 138, 140 and 142, which are employed to accomplish ventricular cardiac pacing by delivery of pulses between electrode 138 and one of electrodes 140 and 142. Electrode 138 is typically located on the distal end of an endocardial lead, and is typically placed in the apex of the right ventricle. Electrode 140 is typically an indifferent electrode mounted on or adjacent to the housing of the cardioverter defibrillator. Electrode 142 may be a ring electrode located on an endocardial lead, located slightly proximal to the tip electrode 138, or it may be a far field electrode, spaced from the heart. Output circuit 108 is controlled by control bus 126, which allows the controller 106 to determine the time, amplitude and pulse width of the pulse to be delivered and to determine which electrode pair will be employed to deliver the pulse.

Sensing of ventricular depolarizations is accomplished by input amplifier 110, which is coupled to electrode 138 and one of electrodes 140 and 142. Signals indicating both the occurrence of natural ventricular contractions and paced ventricular contractions are provided to the controller 106 via bus 128. Controller 106 passes data indicative of the occurrence of such ventricular contractions to microprocessor 100 via control bus 132 in the form of interrupts, which serve to wake up microprocessor 100, so that it may perform any necessary calculations or updating of values stored in random access memory 104.

Optionally included in the device is a physiologic sensor 148, which may be any of the various known sensors for use in conjunction with implantable stimulators. For example, sensor 148 may be a hemodynamic sensor such as an impedance sensor as disclosed in U.S. Pat. No. 4,865,036, issued to Chirife or a pressure sensor as disclosed in U.S. Pat. No. 5,330,505, issued to Cohen, both of which patents are incorporated herein by reference in their entireties. Alternatively, sensor 148 may be a sensor of demand for cardiac output such as an oxygen saturation sensor as disclosed in U.S. Pat. No. 5,176,137, issued to Erickson et al. or a physical activity sensor as disclosed in U.S. Pat. No. 4,428,378, issued to Anderson et al., both of which patents are incorporated herein by reference in their entireties. Sensor processing circuitry 146 transforms the sensor output into digitized values for use in conjunction with detection and treatment of arrhythmias.

External control of the implanted cardioverter/defibrillator is accomplished via telemetry/control block 120 which allows communication between the implanted cardioverter/pacemaker and an external programmer. Any conventional programming/telemetry circuitry is believed workable in the context of the present invention. Information entering the cardioverter/pacemaker from the programmer is passed to controller 106 via bus 130. Similarly, information from the cardioverter/pacemaker is provided to the telemetry block 120 via bus 130.

Figure 4B:
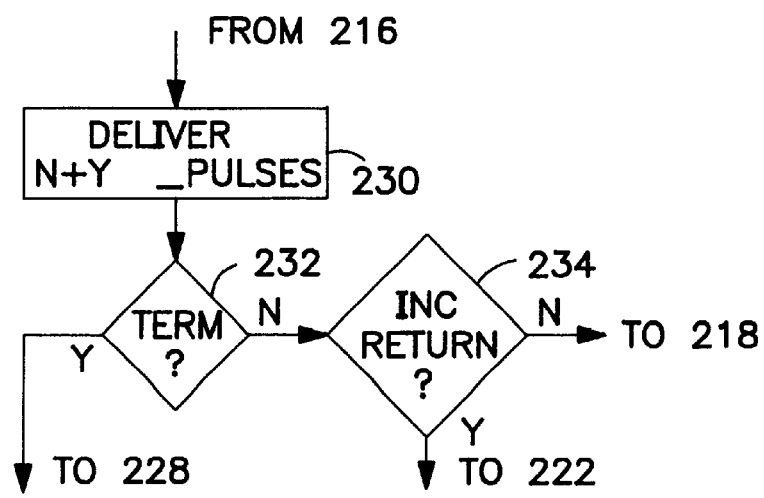
FIGS. 4a and 4b are functional flow charts illustrating the operation of the device illustrated in FIG. 3 according to the present invention.
Figure 4A:
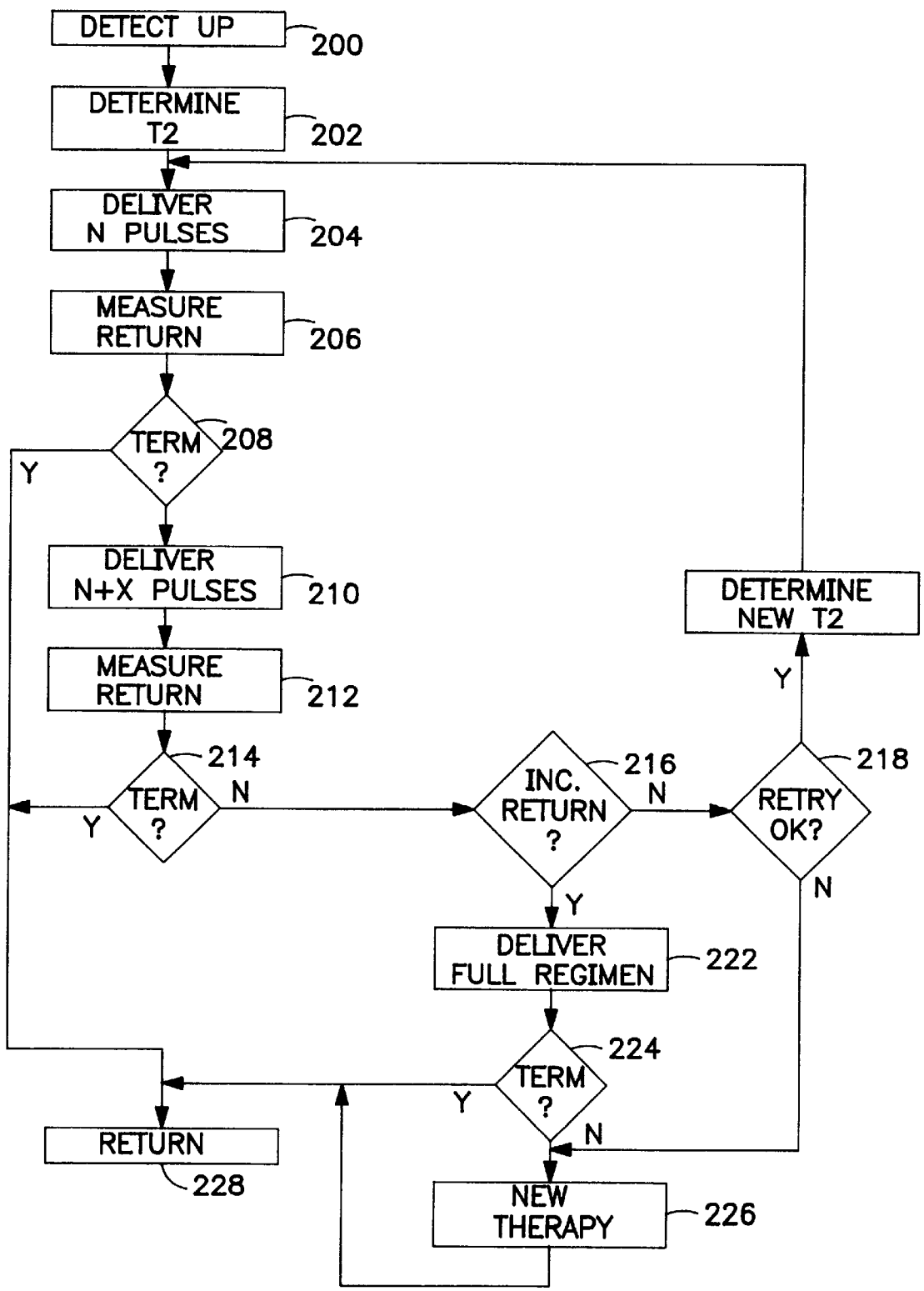

FIGS. 4a and 4b are functional flow charts illustrating the operation of the device shown in FIG. 3. These flow charts are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device, and that providing software to accomplish the present invention in the context of any modern implantable anti-tachycardia pacemaker or implantable pacemaker/cardioverter, given the disclosure herein, is well within the abilities of one of skill in the art.

FIG. 4a is a functional flow chart illustrating the over-all operation of the device in conjunction with practicing the present invention. At 200, the device detects the occurrence of a tachycardia and it determines the first inter-pulse interval T2 for the first scheduled anti-tachycardia pacing regimen. This interval may be a percentage of the average interval separating the spontaneous depolarizations during detected tachyarrhythmia, e.g. about 90%. The device then delivers a sequence of N pulses at 204, where the value of N may be, for example, two to four pulses. At 206, after delivery of the Nth pulse, the return cycle is measured. While it is not believed likely that the tachycardia has terminated, the device nonetheless checks at 208 to determine if it has terminated. Detection of termination of the tachycardia may occur, for example in response to a measured return cycle of greater than a defined duration or in response to a measured return cycle of greater than a defined duration followed by one or more spontaneous R-waves separated by intervals greater than the defined duration. If the tachycardia has terminated, the device returns to normal operation. If the return interval is not indicative of termination of tachycardia, the device delivers a sequence of N+X pulses at 212, where X is typically 1 to 3. The device checks again at 214 to determine whether the tachycardia has terminated. If not, the device compares the measured return cycle to the previously measured return cycle. In the event that the return cycle has increased or increased by more than a preset increment, for example 0 to 200 milliseconds, the device delivers the entire series of pulses programmed for the pulse regimen at 222. If the device then detects termination of the tachycardia at 224, the device returns to normal operation at 228. If termination is not detected at 224, the device schedules the next available therapy, which may be a new pacing regimen or a cardioversion pulse and returns to normal operation at 228 to await re-detection of the tachycardia or detection of termination of the tachycardia.

In the event that following delivery of the series of N+X pulses, an increased return cycle is not detected at 216, the device checks at 218 to determine whether a delivery of a subsequent series of anti-tachycardia pacing pulses is consistent with the programming. Additionally or alternatively, if the device includes a hemodynamic sensor, delivery of a subsequent set of anti-tachycardia pacing pulses may be prevented in response to detection of hemodynamic compromise. If a subsequent series of pacing pulses is not to be delivered, a cardioversion shock or other therapy may be scheduled at 226. If the device programming and/or the hemodynamic sensor allows, however, the device may proceed directly to deliver pacing pulses according to the next scheduled pacing pulse regimen, having modified pulse parameters, in this case an reduced inter-pulse interval as defined at 220. The device may either simply deliver the entire series of pacing pulses as programmed for the next scheduled pacing regimen or, as illustrated, may attempt to determine whether pacing pulses according to the new regimen are likely to terminate the tachycardia as a prerequisite to delivery of the entire pacing regimen.

FIG. 4b illustrates alternative methods of operation according to the present invention. In a first alternative, following a determination that the required increase in return cycle did not occur at 216 (FIG. 4a), the device delivers a series of N+Y pulses at 230, where Y has a value greater than X, and checks for termination of the tachycardia at 232, returning to normal operation at 228 (FIG. 4a). If the tachycardia has not terminated, the device checks at 234 to determine whether the required increase in return cycle length has occurred. If so, the device delivers the entire pacing regimen at 222 (FIG. 4a). If not, the device will check at 218 (FIG. 4a) to determine whether a subsequent pacing regimen is to be delivered. In a second alternative embodiment, the step of delivering N+Y pacing pulses at 230 may occur following a determination that the required increase in return cycle did occur at 216 (FIG. 4a).

In conjunction with the above disclosure, I claim:

1. A method of treating a tachycardia, comprising:
defining a pacing pulse regimen comprising a series of a first number of pacing pulses delivered at a first set of pulse parameters;
detecting a tachycardia;
responsive to detection of the tachycardia, delivering a first series of less than the first number of pacing pulses, having the first set of pulse parameters;
measuring a return cycle time following delivery of the first series of pacing pulses;
delivering a second series of a number of pacing pulses greater than the first series of pacing pulses but less than the first number of pacing pulses, and having the first set of pulse parameters;
measuring a return cycle time following delivery of the second series of pacing pulses;
determining whether the measured return cycle following the second series of pulses exceeded the return cycle following the second series by a required amount; and responsive to a determination that the measured return cycle following the second series of pulses did not exceed the return cycle following the second series by the required amount, delivering an anti-tachycardia therapy other than the defined pulse regimen.

2. A method according to claim 1 wherein delivering an anti-tachycardia therapy other than the defined pulse regimen comprises delivering a cardioversion shock.

3. A method according to claim 1 further comprising employing a hemodynamic sensor to detect hemodynamic compromise and, following deliver of the second series of pacing pulses, in response to detection of hemodynamic compromise, delivering a cardioversion shock.

4. A method according to claim 1 wherein delivering an anti-tachycardia therapy other than the defined pulse regimen comprises delivering a third series of pacing pulses having a second set of pulse parameters different from the first set of pulse parameters.

5. A method of treating a tachycardia, comprising:

defining a pacing pulse regimen comprising a series of a first number of pacing pulses delivered at a first set of pulse parameters;

detecting a tachycardia;

responsive to detection of the tachycardia, delivering a first series of less than the first number of pacing pulses, having the first set of pulse parameters;

measuring a return cycle time following delivery of the first series of pacing pulses;

delivering a second series of a number of pacing pulses greater than the first series of pacing pulses but less than the first number of pacing pulses, and having the first set of pulse parameters;

measuring a return cycle time following delivery of the second series of pacing pulses;

determining whether the measured return cycle following the second series of pulses exceeded the return cycle following the second series by a required amount; and responsive to a determination that the measured return cycle following the second series of pulses did exceed the return cycle following the second series by the required amount, delivering a series of the first number of pacing pulses delivered at the first set of pulse parameters.

6. An apparatus for treating a tachycardia, comprising:

means for defining a pacing pulse regimen comprising a series of a first number of pacing pulses delivered at a first set of pulse parameters;

means for detecting a tachycardia;

means responsive to detection of the tachycardia, for delivering a first series of less than the first number of pacing pulses, having the first set of pulse parameters;

means for measuring a return cycle time following delivery of the first series of pacing pulses;

means for delivering a second series of a number of pacing pulses greater than the first series of pacing pulses but less than the first number of pacing pulses, and having the first set of pulse parameters;

means for measuring a return cycle time following delivery of the second series of pacing pulses;

means for determining whether the measured return cycle following the second series of pulses exceeded the return cycle following the second series by a required amount; and means responsive to a determination that the measured return cycle following the second series of pulses did not exceed the return cycle following the second series by the required amount, for delivering an anti-tachycardia therapy other than the defined pulse regimen.

7. An apparatus according to claim 6 wherein the means for delivering an anti-tachycardia therapy other than the defined pulse regimen comprises means for delivering a cardioversion shock.

8. An apparatus according to claim 6 further comprising a hemodynamic sensor means for detecting hemodynamic compromise and, means for delivering a cardioversion shock following deliver of the second series of pacing pulses in response to detection of hemodynamic compromise.

9. An apparatus according to claim 6 wherein the means for delivering an anti-tachycardia therapy other than the defined pulse regimen comprises means for delivering a third series of pacing pulses having a second set of pulse parameters different from the first set of pulse parameters.

10. An apparatus for treating a tachycardia, comprising:

means for defining a pacing pulse regimen comprising a series of a first number of pacing pulses delivered at a first set of pulse parameters;

means for detecting a tachycardia;

means responsive to detection of the tachycardia, for delivering a first series of less than the first number of pacing pulses, having the first set of pulse parameters;

means for measuring a return cycle time following delivery of the first series of pacing pulses;

means for delivering a second series of a number of pacing pulses greater than the first series of pacing pulses but less than the first number of pacing pulses, and having the first set of pulse parameters;

means for measuring a return cycle time following delivery of the second series of pacing pulses;

means for determining whether the measured return cycle following the second series of pulses exceeded the return cycle following the second series by a required amount; and means responsive to a determination that the measured return cycle following the second series of pulses did exceed the return cycle following the second series by the required amount, for delivering a series of the first number of pacing pulses delivered at the first set of pulse parameters.

* * * * *

UNITED STATES PATENT AND TRADEMARK OFFICE
CERTIFICATE OF CORRECTION

PATENT NO. : 6,167,308
DATED : December 26, 2000
INVENTOR(S) : DeGroot et al.

It is certified that error appears in the above-identified patent and that said Letters Patent is hereby corrected as shown below:

<u>Title page,</u>
Item [75] Inventor: Missing an inventor, should read -- Paul J. DeGroot, Mark E. Josephson. --

Signed and Sealed this

Thirtieth Day of October, 2001

*Attest:*

NICHOLAS P. GODICI
*Attesting Officer      Acting Director of the United States Patent and Trademark Office*